(12) United States Patent
Hauser

(10) Patent No.: US 9,011,934 B2
(45) Date of Patent: Apr. 21, 2015

(54) MULTI-PURPOSE ANTI-ITCH TREATMENT

(71) Applicant: SatisPharma, LLC, Boulder, CO (US)

(72) Inventor: Ray L. Hauser, Boulder, CO (US)

(73) Assignee: SatisPharma, LLC, Boulder, CO (US)

( * ) Notice: Subject to any disclaimer, the term of this patent is extended or adjusted under 35 U.S.C. 154(b) by 0 days.

(21) Appl. No.: 13/917,948

(22) Filed: Jun. 14, 2013

(65) Prior Publication Data

US 2014/0370124 A1    Dec. 18, 2014

(51) Int. Cl.
| | |
|---|---|
| *A61K 33/06* | (2006.01) |
| *A61K 31/14* | (2006.01) |
| *A61K 31/19* | (2006.01) |
| *A61K 31/315* | (2006.01) |
| *A61K 31/4418* | (2006.01) |
| *A61K 31/51* | (2006.01) |
| *A61K 31/52* | (2006.01) |
| *A61K 31/522* | (2006.01) |
| *A61K 31/5375* | (2006.01) |
| *A61K 31/555* | (2006.01) |
| *A61K 31/616* | (2006.01) |
| *A61K 31/618* | (2006.01) |
| *A61K 31/7068* | (2006.01) |
| *A61K 31/714* | (2006.01) |

(52) U.S. Cl.
CPC ............. *A61K 33/06* (2013.01); *A61K 31/14* (2013.01); *A61K 31/19* (2013.01); *A61K 31/315* (2013.01); *A61K 31/4418* (2013.01); *A61K 31/51* (2013.01); *A61K 31/52* (2013.01); *A61K 31/522* (2013.01); *A61K 31/5375* (2013.01); *A61K 31/555* (2013.01); *A61K 31/616* (2013.01); *A61K 31/618* (2013.01); *A61K 31/7068* (2013.01); *A61K 31/714* (2013.01)

(58) Field of Classification Search
CPC .................................................. A61K 31/618
USPC ......................................................... 424/682
See application file for complete search history.

(56) References Cited

U.S. PATENT DOCUMENTS

| | | | |
|---|---|---|---|
| 3,026,248 A * | 3/1962 | Noseworthy et al. | .......... 514/153 |
| 4,784,999 A | 11/1988 | Angersbach et al. | |
| 4,877,773 A | 10/1989 | Turner | |
| 6,197,823 B1 | 3/2001 | Barr et al. | |
| 6,348,501 B1 | 2/2002 | Holt et al. | |
| 6,419,913 B1 * | 7/2002 | Niemiec et al. | ............ 424/78.07 |
| 6,573,302 B1 | 6/2003 | Holt et al. | |
| 6,653,352 B2 | 11/2003 | Barr et al. | |
| 6,693,100 B1 | 2/2004 | Zarmanian et al. | |
| 6,812,254 B1 | 11/2004 | Barr et al. | |
| 7,271,182 B2 | 9/2007 | Kamiyama et al. | |
| 7,709,497 B2 | 5/2010 | Christensen, IV et al. | |
| 7,879,344 B2 | 2/2011 | Feldkamp et al. | |
| 2006/0235080 A1 | 10/2006 | Weissbach et al. | |
| 2007/0258935 A1 | 11/2007 | McEntire et al. | |
| 2007/0269393 A1 | 11/2007 | Wepfer | |
| 2008/0058369 A1 | 3/2008 | Allen et al. | |
| 2008/0255186 A1 | 10/2008 | Christensen et al. | |
| 2008/0275078 A1 | 11/2008 | Cook et al. | |
| 2009/0053290 A1 | 2/2009 | Sand et al. | |
| 2009/0123504 A1 | 5/2009 | Feldkamp et al. | |
| 2009/0318494 A1 | 12/2009 | Allen et al. | |
| 2009/0325952 A1 | 12/2009 | Allen et al. | |
| 2011/0184016 A1 | 7/2011 | Lerner et al. | |
| 2013/0085166 A1* | 4/2013 | Makra | ........................ 514/352 |

FOREIGN PATENT DOCUMENTS

WO    2011/075688 A1    6/2011
WO    2011/086458 A1    7/2011

OTHER PUBLICATIONS

Burke (Solubility Parameters: Theory and Application. The Book and Paper Group Annual. vol. III. (1984)).*

* cited by examiner

*Primary Examiner* — Jake Vu
(74) *Attorney, Agent, or Firm* — James A. Sheridan

(57) ABSTRACT

There is disclosed a formulation of a transdermal skin treatment effective in inhibition of itch sensation. In an embodiment, the formulation includes a solvent mixture of alcohols, glycols and water combined to provide a solubility parameter between 20 $Pa^{0.5}$ and 40 $Pa^{0.5}$, the solvent mixture having an average normal boiling temperature of at least 100° C., the solvent mixture having at least 0.04 mols/liter of multivalent cations, the solvent mixture containing at least one local anesthetic, and the solvent mixture having pH exceeding 8.0, with a thixotropic flow characteristic accomplished by an organic gellant. Other embodiments are also disclosed.

23 Claims, 1 Drawing Sheet

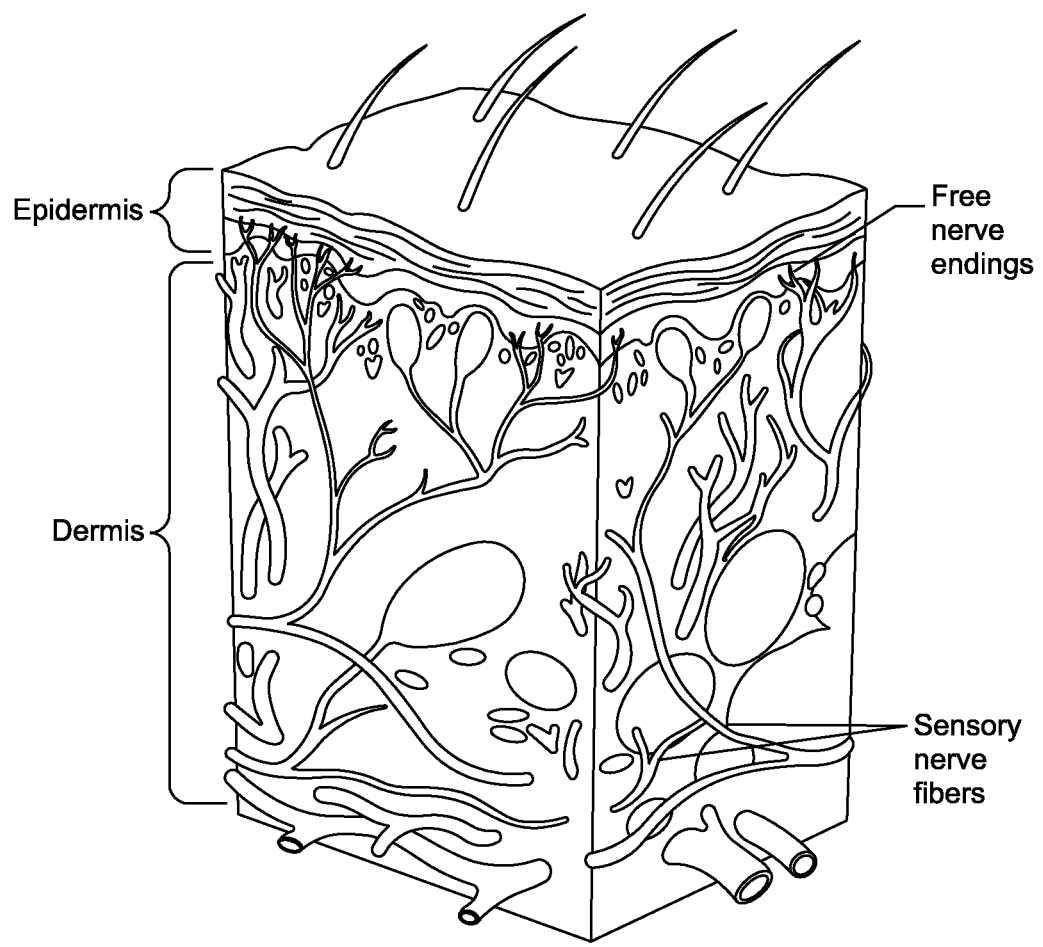

MULTI-PURPOSE ANTI-ITCH TREATMENT

BACKGROUND

Antipruritics (anti-itch medications) have been used for years for a variety of causes, but the world lacks a safe treatment that will provide relief for most or all of these nuisance or painful conditions.

Antihistamines such as diphenhydramine (Benadryl), corticosteriods such as 1% hydrocortisone cream on the OTC market and Topicort 0.25% or 0.05% desoxymetasone by prescription, local anesthetics such as benzocaine topical cream (Lanacane®), and counter-irritants such as mint oil, menthol or camphor have been used. Dilute ammonium hydroxide is marketed for use on mosquito bites, where it can neutralize the acid component of the sting. Benzyl alcohol and pramixine hydrochloride are often used at 10% and 1% concentrations respectively. Benadryl® is an itch stopping spray containing active ingredients identified as diphenhydramine hydrochloride 2% as a topical analgesic and zinc acetate 0.1% as a skin protectant, and reference is made to its use for insect bites, poison ivy, mosquito bites, sunburn and minor cuts and scrapes.

Most of these skin treatments use a small amount of active ingredients in a medium of mineral oil or petroleum jelly, such as Vaseline brand petroleum jelly, or water as the carrier. Glycerol (as named by chemists) or glycerin (as it is called by pharmacists) and propylene glycol are used as carriers for the active ingredients in some commercial skin treatments. Water is a frequent component or main carrier, as in the case of Epsom salts (i.e., magnesium sulfate or magnesium sulphate) or ammonia.

Hydrocortisone creams are used commonly as multi-purpose treatments for itching, but these creams often have severe adverse side effects. Packages of Over the Counter (OTC) hydrocortisones generally indicate to discontinue use after 1 week, but even dermatologists prescribe longer term usage for skin problems such as eczema. Unfortunately, continued use of these steroids can lead to addiction and higher dosages are needed to obtain relief, until the patient experiences what some call "elephant skin" and very painful withdrawal, with oozing, shedding and itching can last up to 24 months for complete recovery and return to normal skin. The International Topical Steroid Addiction Network addresses recovery from this problem at www.itsan.org. Drs. Marvin Rapaport and Mototsugu Fukaya have treated thousands of patients undergoing painful withdrawal from such addiction in the U.S. and in Japan. "Corticosteroid Addiction and Withdrawal in the Atopic: The Red Burning Skin Syndrome" discusses this topic in detail in *Clinics in Dermatology*, 2003; 21:201-214. Thus, there is now a desperate need for a multi-purpose safe alternative to the use of corticosteroids.

Antihistamines are used sometimes for treatment of bee and wasp stings, as these often cause allergies. Some folks are allergic to Benzocaine in products such as Lanacane, which sometimes is a cause for itching of skin or headaches, according to the Mayo Clinic.

Calamine lotion and Epsom salt solutions have been used for many years for treatment of itching skin; their limitations and possible benefits are discussed below.

The chemistry for some of the itch causes is known, and it remains a mystery for some. The leaves of poison ivy, poison sumac and poison oak, for example, are known to transfer urushiol to the skin. Urushiol is a catechol (double hydroxyl groups on a benzene ring) with an adjacent hydrocarbon with 15 to 17 carbons, some saturated, some with single, double or triple unsaturation groups.

Both the acid and the unsaturation groups may be responsible for the itching of this compound. Potassium permanganate was once recommended as a treatment for poison ivy, perhaps intended to oxidize the unsaturations. This purple coloration transitioned quickly to brown manganese oxide and was less effective than desired on the young skin of this inventor seventy five years ago. Rapid treatment with soapy water (within 10 minutes of contact) can prevent the rash of poison ivy, but wash basins are rare along hiking trails. In contrast to the "unsaturation" theory, linseed oil has been used for many years without causing irritation such as poison ivy.

U.S. Pat. No. 5,443,847 discloses a treatment for poison ivy using divalent manganese compounds in aqueous solution. The patent states that divalent manganese ions couple with the ortho-position hydroxyl radicals and thereby detoxify the urushiol. If true, this might be the mechanism for effectiveness with other multivalent cations such as magnesium, calcium and zinc for this specific skin injury.

Insect bites and stings usually inject one or more nasty chemicals into the blood. A female mosquito does damage by injecting her saliva into the victim's blood steam in order to reduce the blood's viscosity for an easier suck back into her belly. Mosquito saliva contains about 20 proteins, including components to minimize vascular constriction, blood clotting, and platelet aggregation, and enzymes that aid in sugar feeding. Female biting midges (Dipteran), often called sand flies, also need protein from animal blood for their eggs. They often carry viruses or visceral leishmaniasis, a parasite almost as deadly as malaria. Spider bites may introduce a venom into the skin.

The itch from Psoriasis can be very painful and the sources can sometimes be life-threatening. This invention does not presently claim to heal any diseases associated with itching, but neither does it preclude such possibilities, and future clinical tests may show such efficacy. However, a number of users of the Example formulations cited below have brought appreciative response from users who have treated a variety of ailments and injuries to the skin.

Persons affected by shingles would hardly call their pain an itch. This herpes zoster is known to be caused by surprising reactivation of dormant virus from chicken pox many years earlier in one's life. Rashes and blisters may form along with the very painful viral attack on nerve ends. Treatments may include antivirals such as acyclovir, famiclovir and valacyclovir, taken in pill form or by intravenous injections, and corticosteroids may be attempted to reduce swelling and local pain. An online reference from the National Institutes of Health mentions that calamine lotion, colloidal oatmeal or starch baths may help to relieve the itching and discomfort (ref. www.ncbi.nlm.nih.gov/ubmedhealth/PMH0001861/).

The old-time anti-itch treatments of Epsom salts (magnesium sulfate solution in water) and calamine lotion (calcium hydroxide solution, and zinc oxide dispersion in water, sometimes with a tint of ferric oxide) are of particular interest. This inventor suspects that these formulations are very limited in ability to deliver any useful chemicals to nerve endings. Their deficiencies are in the use of water for delivery of the cations. Water does not readily penetrate the skin, lest swimmers and bathers become balloons or become Michelin Men. These multivalent cations are shown by this invention to be more effective when delivered by a carrier in which they are soluble that can penetrate the epidermis barrier better than water.

The USP formula for calamine lotion is as follows:
Zinc oxide, 80 grams
Bentonite magma, 250 ml (thickener)
Glycerin, 20 ml
Calcium hydroxide, saturated (1.7 gm) solution in water to make 1 liter This liter of solution has only 0.022 mols of calcium and virtually no zinc ions in a water/glycerin solution which has an effective solubility parameter of 46.5 $Pa^{0.5}$. The zinc oxide is insoluble, thus forms no zinc ions and can not permeate the epidermis to reach nerve endings. Thus the zinc ion is expected to have negligible effect on any nerve endings, but a small amount of calcium ion might penetrate the skin barrier and reach nerve endings, as a small amount of water penetrates the epidermis.

Epsom salt (magnesium sulfate heptahydrate) has been known since 1618 when Henry Winkler in Epsom, England, promoted its natural waters used as a "feel good" bath. Calamine lotion has been known in the U.S. since the early 1830s and has been used as a home treatment for a variety of itches. In 1992 the Federal Drug Administration declared that it had not been proven to be effective and banned it from the market with any healing claims. In 2008, the FDA relented to recognized usage and approved its use as a "skin protectant" for treatment for plant poisons, but with no clarification whether the calcium or the zinc component or the combination of these was Active.

The historical effectiveness of these two products, though used in the disadvantageous medium of water, raises the issue of why has not research occurred within the multi-million-dollar budgets of companies in the skin care business. Insight into this history and into the physical chemistry of mass transfer through the epidermis has provided the stimulus for creation of new formulations described herein.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

In an embodiment, there is provided a formulation of a transdermal skin treatment effective in inhibition of itch sensation, the formulation comprising:

a solvent mixture of alcohols, glycols and water combined to provide a solubility parameter between 20 $Pa^{0.5}$ and 40 $Pa^{0.5}$, the solvent mixture having an average normal boiling temperature of at least 100° C., the solvent mixture having at least 0.04 mols/liter of multivalent cations, the solvent mixture containing at least one local anesthetic, and the solvent mixture having pH exceeding 8.0, with a thixotropic flow characteristic accomplished by an organic gellant.

Additional objects, advantages and novel features of the technology will be set forth in part in the description which follows, and in part will become more apparent to those skilled in the art upon examination of the following, or may be learned from practice of the technology.

BRIEF DESCRIPTION OF THE DRAWING

Non-limiting and non-exhaustive embodiments of the present invention, including the preferred embodiment, are described with reference to the following FIGURE, wherein like reference numerals refer to like parts throughout the various views unless otherwise specified.

FIG. 1 illustrates a schematic view of the epidermis and dermis.

DETAILED DESCRIPTION

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

The inventor proposes two theories regarding the effectiveness of new Formulations. Sodium and potassium ions are known to attach to nerve endings and to send signals to the brain. Thus, the nerve endings are known to have negative charges. Multi-valent cations are theorized to compete successfully with sodium and potassium ions at nerve endings, perhaps forming electrical short-circuits by locking onto two or three nerve endings per cation (for divalent or trivalent cations, respectively) and, thus, preventing communication of a nerve stimulation to the brain in the normal manner. If the few penetrating calcium, zinc and magnesium cations from aqueous calamine lotion and Epsom salt solutions can be effective in relieving pain, the much higher delivered concentrations of the disclosed new formulations can be much more effective. The second theory relates to the duration of attachment of the multivalent cations, which derives from the usual 12-24 hour relief from skin irritation with the formulations described and claimed herein. Multivalent cations are known to crosslink polymers to form ionomers. They are also known to become solvated by chelates, forming stable complexes. The duration of pain relief may relate to either of these effects at nerve endings. Nerve endings are illustrated as dendrites and they may well have chelate-type wraps around multivalent cations.

These heretofore unknown insights and theories have not been found in academic or governmental presentations.

The formulations in the Examples and their functional characteristics in Table 1 below are evidence of novelty, and they attest experientially to the rationality of these theories.

Treatments for the itching from insect bites, plant poisons and other causes are regulated for OTC sales by restrictions in 21 Code of Federal Regulations, with specifics on acceptable and unproven active ingredients. Many ingredients are listed as safe but with unproven efficacy as skin treatments or protectants in CFR 21.310.545, including calcium hydroxide and magnesium sulfate which are mentioned in the NIH publication referenced above. Thus, the U.S. Food and Drug Administration teaches against unproven use of many such chemicals in treatments for itching of skin and the FDA disallows any claims of efficacious performance unless proven by clinical studies.

Various embodiments disclosed herein involve unique combinations of "functional ingredients" along with liquid carriers that can convey these functional ingredients through the skin barrier to reach nerve endings where the functional ingredients can ameliorate irritations and itchings. The functional ingredients are chosen to provide a variety of inhibitory characteristics for overlapping time periods for a variety of causes of pain. The functional ingredients are used in concentrations defined by their solubility in the carriers which are selected for the formulations. The liquid carriers are specifically selected for attributes of skin permeability, quantifiable solubility characteristics, and vapor pressure or evaporation characteristics.

Embodiments start with liquid carrier systems which are known to penetrate the skin readily. Glycerol (glycerin), propylene glycol, and propylene carbonate are known to penetrate the skin safely. Glycerol and propylene glycol also double as humectants, retaining and/or adding atmospheric water to dry skin over a period of hours. Propylene, butylene and glycerol carbonates are aprotic solvents (and can provide unique electrolytes with ionic compounds) which may have a unique effect on nerves. Dimethyl sulfoxide is known to penetrate the skin more quickly, but not safely, and it has been banned for use in humans. Nicotine is suspected to penetrate mucous membranes very quickly, as in the first puff from a tobacco cigarette. A mixture of solvents is preferred in order to obtain synergism of solvency.

Transcutanol (Diethylene glycol monoethyl ether) and isopropyl myristate are two common and preferred transdermal permeants, but they are not good solvents for ionic compounds. Theses carriers may assist in small quantity with the above carrier liquids, but are not effective as the principal carriers of multivalent cations in the formulation.

The polyols described here have the advantage of slow evaporation, prompting the disadvantage of remaining slightly tacky on the skin after application. Triethanolamine, a small amount of colloidal oatmeal, or both, has been found to counteract this feeling by giving a smooth, non-tacky surface on the skin.

Various embodiments add multivalent compounds to the carriers in forms that are soluble in the liquid carrier system. Acetates are one form, thus magnesium, calcium and zinc acetates have been found to have acceptable solubility in glycol mixtures. These divalent compounds are surprisingly discovered to be relatively long-term anti-pruritics, with effectiveness a day or more when administered in the above solvent system (in contrast to their historical use in aqueous solvents). Magnesium sulfate is also soluble in these polyols. Calcium nitrate is soluble at higher concentrations in alcohols than its acetate and is a prospective divalent cation for the anti-itch treatment. It is slightly acidic and it may be inappropriate for a person using erectile disfunction medications who is advised to avoid nitrates less they cause a decrease of blood pressure. Various embodiments also add short-term antipruritics, such as salicylates, considered to be NSAID compounds (Non-Steroidal Anti-Inflammation Drugs), also known as analgesics. Methyl salicylate is an effective solvent which adds pain suppression and a pleasant (to some people, while objectionable to some) medicinal smell. Acetyl salicylic acid (aspirin) is also considered by some to be an effective short-term antipruritic administered directly to the site of the itching in the above solvent system, but the FDA has not yet accepted proof of efficacy for topical applications of aspirin. Trolamine salicylate is an equimolar combination of trolamine (triethanolamine) and salicylic acid and is not an approved active ingredient, but may have some pain-killing effect as well as a smooth feeling on the skin in one embodiment. Trolamine and aspirin may be added separately to provide these combined effects.

An immediate, but short-term anti-itch effect can be accomplished by dissolution of a local anesthetic such as benzocaine, novocaine, or lidocaine in the carrier.

Many chemicals that cause itching also cause skin damage, and a healing lotion, such as aloe vera, is a desirable component. In case there is any infection of the itching area (possibly caused by scratching) the presence of an antibiotic such as zinc bacitracin, benzalkonium chloride, or benzethonium chloride may be worthwhile. Isopropyl alcohol is an effective topical antiseptic as well as a good solvent for the mix.

Sodium hypochlorite is an effective disinfectant (within the packaged skin lotion and on the skin) as well as a moderately strong alkali to counteract acidic irritations such as plant poisons.

DEET (N,N-Diethyl-meta-toluamide) can be effective in repelling mosquitoes when this chemical is used as a preventive. Though not an anti-itch treatment, it may be a useful component in an anti-itch formulation that may be carried while hiking, camping or fishing. DEET is conventionally used as a 25% concentration in a spray. Citronella Oil is another insect repellant, sometimes used at 5% concentration in sprays.

In order to counteract the acids of insect bites and plant poisons, the universal itch treatment should have an alkaline pH, preferably 8 or above. Triethanolamine is an effective and safe alkaline and it is also an effective solvent. The pH can be further adjusted by addition of a safe and effective base such as sodium bicarbonate, sodium hydroxide, sodium hypochlorite, magnesium hydroxide, or sodium tetraborate. Water is an effective diluent for this multi-purpose, almost universal anti-itch treatment. Within the formulation it can provide thixotropy for a cream or gel and on dry skin it is a moistener.

A number of gellants can provide a thixotropic flow characteristic to the skin lotion so that it can be applied smoothly without dripping. Minerals such as fumed silica and bentonite form complexes with water to provide useful thixotropy, but these minerals leave a white residue when the liquids have evaporated or permeated. Organic gellants such as gelatin, guar gum, acrylic polymers and xanthan gum also gel water-containing formulations when used carefully. However, gelatin has a relatively abrupt transition between moderate viscosity and a hard gel, guar gum becomes sticky, and gels of acrylic polymers don't survive when multi-valent cations are present. Xanthan is the preferred gellant when first dispersed in an alcoholic medium (glycerin, propylene glycol, etc.) and then dispersed in water.

One embodiment can avoid the use of water (except the water of hydration in the soluble salts) and thus maximize delivery of functional chemicals to nerve endings. This may be of particular value in treatment of pain from Topical Steroid Addiction.

Anti-viral compounds such as acyclovir, famiclovir and valacyclovir are expected to be soluble in the solvent systems described above, for direct treatment of the pain from herpes zoster (shingles) and one or more of these may be included in an embodiment.

Pramoxin or pramoxin hydrochloride may be added as an additional topical anesthetic in one embodiment. These two medications are known to provide short-term relief from itching by stopping nerves from sending pain signals In one embodiment, anti-fungals may be incorporated to help treat "jock itch," athletes' foot, toenail fungus and other irritations. Among the many fungus treatments, preference is given toward zinc undecylenate, potassium sorbate, ciclopirox-ethanolamine, tolnaftate, and zinc pyrithione. Undecylenate is approved by the FDA in concentrations of 10-25% in accord with 21CFR par 333.2190 and tolnaftate is approved at 1% concentration. Potassium sorbate is a good mold and yeast inhibitor that is very soluble in water and alcohols in various embodiments. Ciclopirox is a broad spectrum anti-mycotic with some anti-bacterial activity, and zinc pyrithione is effective against strep and staph bacteria.

In one embodiment, Vitamins B-1 and B-12 may be added to the formulation in hopes of improving the mixture's long-term performance for treatment of Diabetic Nerve Pain.

Depending upon the nature of packaging and application, embodiments may include the universal anti-itch treatment prepared as a solution with low viscosity, to be applied by spraying onto the affected area, or with higher viscosity for spreading as a cream, gel or lotion. The spray may be formulated to deliver a stable foam to the skin surface. The anti-itch treatment can be applied as a medicated wipe or pledget. When the treatment is applied as a lotion, a higher viscosity is desired than for a spray, and this can be accomplished by the addition of organic gellants similar to xanthan gum, gelatin, or guar gum, or inorganic gellants such as fumed silica or bentonite. An adhesive patch may also be used for applying this medication of various embodiments, as described by U.S. patent application Ser. No. 12/548,301, "Pressure-Sensitive Adhesive for Skin Surface and/or Transdermal Substance Delivery." By addition of hardening polymers such as polyvinylpyrrolidone or polyvinyl alcohol a "stick" applicator is perceived, with hardness or spread comparable to that of lipstick, but this would have much less solvent for conveying the active ingredients through the skin. This would be a difficult formulation. A roll-on applicator is another embodiment, such as used for application of anti-perspirants.

When any healing claims are made for a skin treatment, the Food and Drug Administration requires that labels include listings of active ingredients (AI) which must be listed on approved monographs for the labeled usage, and inactive ingredients, often called excipients. The inactive ingredients may include carrier solvents, diluents, surfactants, preservatives, colorants, perfumes and other components known to be safe.

Table 1 outlines prospective combinations of ingredients, their functions and ranges of concentrations.

TABLE 1

| Functional Ingredient (FI) | Function(s) | Concentration Range, wt. % |
| --- | --- | --- |
| Glycerol (glycerin) | Solvent for Functional Ingredients Transmission of FI through skin Humectant Slow evaporation | 0-20 |
| Propylene carbonate | Solvent for Functional Ingredients Electrolytic Conductivity | 0-30 |
| Propylene glycol | Solvent for Functional Ingredients Transmission of FI through skin Humectant Slow evaporation | 0-30 |
| Diethylene glycol monoethyl ether | Solvent for Functional Ingredients Transmission of FI through skin Humectant Slow evaporation | 0-20 |
| Isopropanol | Solvent for Functional Ingredients Topical antiseptic | 1-20 |
| Methyl salicylate | Solvent for Functional Ingredients NSAID, Pain reliever Pleasant medical odor | 2-20 |
| Chelate, e.g. disodium EDTA | Alkalinity Preservative | 0.5-3 |
| Triethanolamine | Solvent for Functional Ingredients Alkalinity, Smooth skin | 0.5-10 |
| Water | Moistens skin Provides thixotropy | 1-20 |
| Aloe vera gel, 20X | Skin healer | 0.5-5 |
| Acetyl salicylic acid | NSAID, Pain reliever, FI | 0.5-5 |
| Lidocaine | Fast local anesthetic, FI | 0.05-3 |
| Benzocaine | Fast local anesthetic, FI | 0.05-3 |
| Surfactant (e.g. sodium lauryl sulfate, Triton X100, polysorbates | Emulsification of oils Assist transmission through skin | 0.05-2 |
| Linoleic acid | Assist skin healing | 0-2 |
| Preservative (e.g. potassiumsorbate, sodium benzoate) | Stabilize formulation Alkalinity | 0.01-2 |

TABLE 1-continued

| Functional Ingredient (FI) | Function(s) | Concentration Range, wt. % |
| --- | --- | --- |
| Alkaline salt | Adjust pH preferably 8-9 | |
| Gellant | Adjust viscosity appropriate for method of application | 0-5 |
| Benzethonium chloride | First aid antiseptic, FI | 0-0.5 |
| Zinc acetate•2H20 | Multiivalent cation, soluble, FI | 0-5 |
| Magnesium sulfate | Multiivalent cation, soluble, FI | 0-5 |
| Calcium acetate | Multiivalent cation, soluble, FI | 0-5 |
| Oat colloid | Smooth feeling, FI | 0.5-5 |
| Sodium hypochlorite | Alkalinity, disinfectant, smooth feeling | 0-1 |
| Anti-fungal | Combined fungal and bacterial kill | 1-25 |

The term Functional Ingredient as used here in Table 1 does not imply that it meets the definition and usage of Active Ingredient by the Food and Drug Administration, which states specific concentrations or concentration ranges for specific chemicals.

Twelve of the ingredients listed in Table 1 are uniquely multi-functional as used in various embodiments. Not only are these ingredients individually multi-functional, but these ingredients are additive and may be synergistic in their effects.

Coloring agents, perfumes and preservatives (e.g. ethylhexylglycerin) can be added to the medicated formulation as desired, as known by those skilled in cosmetic arts.

A key to the effectiveness is the use of a solvent system having solubility characteristics suitable for the mixture of active ingredients. It has been observed that a mixture of solvents covering a range of solubility parameters is often better than a single solvent for many solutions. Solvency can be characterized by a solubility parameter which is related to the "cohesive energy density" of a solvent, of a solute or both. These are Hildebrand or Hansen solubility parameters which are noted in Table 2 along with the normal boiling temperatures of the solvents in Table 1:

TABLE 2

Solubility Parameters of Individual Liquids

| Component | Solubility Parameter, $Pa^{0.5}$ | Normal Boiling Temp. °C. |
| --- | --- | --- |
| Glycerin | 33.7 | 290 |
| Propylene carbonate | 27.2 | 242 |
| Propylene glycol | 25.7 | 188 |
| Diethylene glycol ethyl ether | 20.8 | 198 |
| Isopropyl alcohol | 18.0 | 82 |
| Methyl salicylate | 21.7 | 223 |
| Triethanolamine | 36.7 | 335 |
| Water | 47.7 | 100 |

The solubility parameter of a mixture is calculated by summing the partial volume contributions:

$$\delta_m = \Sigma V_i \delta_i$$

where $\delta_m$ is solubility parameter of the mixture, $V_i$ is volume fraction of each component and $\delta_i$ is the solubility parameter of the respective component.

Thus the solubility parameter of some of the examples of mixed solvents have been computed by this equation in Table 5 below. The water and isopropanol in these formulations serve as cost-effective diluents that evaporate fairly quickly after application of treatment to the skin, and the other liquids serve as principal carriers of the Functional Ingredients through the skin to nerve endings.

With respect to various embodiments, pain killers are classified by the National Institutes of Health as analgesic compounds. These may be NSAIDS which are non-steroidal anti-inflammatory drugs such as aspirin, naproxen and ibuprofen. Acetaminophen is a different type of analgesic. A multivalent cation may be defined as a medically acceptable ion of beryllium, magnesium, calcium, strontium, barium, copper, iron, manganese, zinc, boron or aluminum. An alkaline compound has a pH in water exceeding 7.0. The term antibiotic is used here in its broader meaning as any medication known to kill germs. A gellant is an additive in small quantity (generally less than 5%) that significantly increases the viscosity of the mixture, preferably with a thixotropic character (having a higher viscosity at low shear rates and lower viscosity at higher shear rates). A preservative may be benzoic acid esters, parabens, a nitrite, sulfite, phenoxy ethanol, anti-oxidant or other chemical known to help prevent chemical or biochemical changes during storage, and is classified as generally recognized as safe. A surfactant is a chemical that can be added in low concentration to significantly decrease the surface tension of a solution; it may be cationic, nonionic or anionic. Examples are soaps, sulfonates, polysorbates and ethoxylates.

As mentioned above, solubility parameters are frequently used to characterize solvency characteristics of different liquids and other organic chemicals. In general, the higher the solubility parameter, the greater the polarity. Water is the highest and fluorocarbons are the lowest among solvents. Joel Hildebrand and then Charles Hansen have developed the concept of solubility parameters, starting with a calculation related to the energy of evaporation per volume in units of (energy/volume)$^{0.5}$ which was later related to polymer/solvent interaction coefficients by Flory and others. Allan Barton has published a listing of many solubility parameters in *CRC Handbook of Polymer-Liquid Interaction Parameters and Solubility Parameters*. Diversified Enterprises has published a table of solvent data at www.accudynetest.com/solubilty_table.html.

The inventor was an early publisher on the topic of solubility parameter with a graduate thesis in 1952 and publication "Swelling of Silicone Elastomers" at *Industrial & Engineering Chemistry*, 48 pp 1202-1208, 1956.

U.S. Food and Drug Administration Regulations

The use of topical medications is highly regulated by the USFDA to insure safety and efficacy of marketed products for both prescription and OTC (Over the Counter) use. As mentioned above, 21 CFR lists most of these regulations, and the Apr. 11, 2012 revision of 21CFR310.545(a) lists many ingredients that are noted in various embodiments. Table 3 lists these with the statement, " . . . based on evidence currently available, there are inadequate data to establish general recognition of the safety and effectiveness of these ingredients for the specific drug products."

TABLE 3

Ingredients not allowed for specific claimed uses without further evidence, with paragraph number and Usages

| Ingredient | 1. Acne | 7. Seborrheic products | 10iv Diaper Rash | 10vi & 18v Insect bite and sting | 10v & 18vi Poison Ivy, Oak, Sumac | 10i External Analgesic |
|---|---|---|---|---|---|---|
| Aspirin | | | X | | X | X |
| Benzocaine-Lidocaine | X | | | | X | |
| Benzethonium chloride | | X | | X | | |
| Calamine | | | | X | X | |
| Calcium acetate | | | | | X | |
| Calcium undecylenate | | X | | | | |
| Glycerin | | | X | | X | |
| Diphenhydramine HCl | | | | | | |
| Isopropanol | | | | | X | |
| Magnesium sulfate | X | | | | | |
| Methyl salicylate | | X | X | | | |
| Salicylic acid | X | | | | | |
| Sodium borate | | X | | X | | |
| Sodium bicarbonate | X | | | | | |
| Trolamine | | | | X | X | |
| Trolamine salicylate | | | | X | | |
| Zinc acetate | | | X | | X | |

This reference to calamine doesn't distinguish between the calcium hydroxide and the zinc oxide components, but other paragraphs refer to the zinc oxide content thereof. Colloidal oatmeal is not really a colloid, as its particle size is usually several microns diameter, and it is not really a medication, but a powder that can leave a smooth surface on the skin. A truly colloidal oatmeal may some day become available, perhaps accomplished by jet milling of the conventional powder. Trolamine is a common pharmaceutical term for triethanolamine.

The FDA gets more specific in other paragraphs which are called "monographs" listing what the organization considers to be acceptable Active Ingredients in OTC formulations that are labeled to treat specific conditions. Sometimes the concentration ranges are specified. Only a few combinations of Active Ingredients are allowed. Formulations that do not fit within the monographs are required to go through the process of new drug approvals with documentation of safety and effectiveness for any and all claims made in labels, in advertising and on web sites.

Table 4 lists the allowed active ingredients for a number of specific monographs.

TABLE 4

| Ingredient | 333.210 Anti-fungals | 333.301 Acne | 346.14 Anorectal Topical | 347.10 Skin Protectant | 347.20 Skin Protectant Combination |
|---|---|---|---|---|---|
| Benzocaine-Lidocaine | | | 2-5% | | X |
| Benzylkonium chloride | | | | | X |
| Calamine | | | | 1-25% ZnO | |
| Colloidal Oatmeal | | | | >.007% | With mineral oil |
| Glycerin | | | 10-45% | 20-45% | X |
| Diphenhydramine | | | | | X |
| Isopropanol | | | | | X |
| Salicylic acid | | 0.5-2% | | | |
| Sodium bicarbonate | | | | X | |
| Tolnaftate | >1% | | | | |
| Zinc acetate | | | | 0.1-2% | |
| Undecylenates | 10-25% | | | | |

None of this list of ingredients is allowed in the categories of Antibiotic (Par 333.110).

Par 347.50 permits labeling for poison ivy for skin protectant products containing zinc acetate only at a specific concentration range. Colloidal oatmeal is not approved for use with glycerin or liquids other than mineral oil. Oatmeal oil and methyl salicylate are not mentioned in these FDA monographs.

The FDA permits limited combination of active ingredients as skin protectant in Paragraph 347.10, e.g. cocoa butter, cod liver oil, hard fat, lanolin, mineral oil or petrolatum may be combined with "caine" type anesthetics, alcohols and antihistamines. It is unclear whether glycerin is included among the permitted alcohols It is notable that magnesium sulfate is not listed as an approved active ingredient in any of these OTC monographs, despite the long history of Epsom salts as an itch relief. Likewise, salicylates are not considered to be efficacious active ingredients. Zinc acetate can be considered an active ingredient (at specified concentrations) as a skin protectant formulation labeled for treatment of poison ivy, but not for insect bites or stings. Both magnesium sulfate and calcium sulfate are specifically delisted as active ingredients for all categories.

The combinations of Functional Ingredients in various embodiments are thus unique and are banned from claims as Active Ingredients by the FDA without further evidence that they are proven to be effective in treatments of specified skin conditions by clinical studies. The FDA specifically teaches against any claims for the novel formulations of various embodiments disclosed herein which use unapproved mixtures of unapproved functional ingredients in unapproved mixtures of carriers.

Informal experiential tests to date have shown these combinations to be effective, and clinical tests are anticipated in the future that may satisfy the FDA requirements and which may expand the scope of the formulations.

The FDA does not recognize the characterization of a multi-purpose itch relief and the FDA teaches away from using the combinations of ingredients disclosed herein for multi-purpose itch relief.

Example 1

A simple treatment for topical eczema was prepared by dissolving calcium nitrate tetrahydrate in isopropanol. When applied to the skin once per day it effectively and quickly stopped the itching and an eczema rash disappeared within a few days. The molal concentration of calcium ion in isopropanol was about 0.75, and the alcohol water solubility parameter was about 21.6 $Pa^{0.5}$ including addition of the hydrated salt to the alcohol.

Example 2

A simple anti-itch treatment was prepared and was applied to skin badly affected by actinic keratosis on legs of the inventor. Whereas the dermatologist had prescribed Topicort (a corticosteroid) applied twice daily, it was first found that a saturated solution of Epsom salts (magnesium sulfate heptahydrate) in glycerol was equally effective in treatment of itching, even though applied once daily. It was surprisingly found that the keratosis spots disappeared within a week and the skin cleared up. Unfortunately, the glycerol left a wet, sticky surface on the skin until it evaporated or was absorbed into the epidermis. A smooth, nonsticky surface is more desirable. The saturated solution was about 0.4 molal magnesium ion and the hydrated salt adjusted the solubility parameter to about 35.2 $Pa^{0.5}$. The pH was slightly acidic.

Example 3

A multi-purpose anti-itch treatment was prepared with the following recipe:

Glycerol, 20 gm; Propylene glycol, 30 gm; Ethoxy diethylene glycol, 20 gm; isopropanol, 15 gm; water, 25 gm; Methyl salicylate 10 gm; Triethanolamine, 10 gm; Aloe vera gel, 5 gm; Sodium lauryl sulfate, 0.2 gm; Zinc acetate hydrate, 2 gm; Calcium acetate hydrate 2 gm; Magnesium acetate tetrahydrate, 2 gm; Acetyl salicylic acid, 4 gm; Tetrasodium EDTA, 2 gm; Zinc bacitricin, 0.2 gm; Lidocaine, 0.2 gm; Sodium Benzoate, 0.5 gm; Sodium acetate, 1.35 gm; Fumed silica (Cab-O-Sil) 5 gm. The components were dissolved in the solvent mixture and the silica was dispersed with high speed agitation. This formulation had a pH measured to be about 9 and had a viscosity suitable for manual application to the skin and retention without dripping. It contained multivalent cations in solution at 0.25 molal concentration, and the solubility parameter of the solution was 33.6 $Pa^{0.5}$.

A field hydrologist used a sample of Example 3 for treatment of chigger bites around the ankles and found it to be very effective, very quickly, in reducing the itch from the chiggers.

Example 4 This is a variation of Example 3 with the exception that propylene carbonate was used in place of glycerol and no sodium acetate was included. This aprotic solvent is also an effective electrolyte and may have special beneficial effects on the ends of nerves. It may be especially beneficial for folks suffering from shingles. Propylene carbonate does not leave a sticky feeling on the skin. The solubility parameter of this liquid mixture was calculated to be 25 $Pa^{0.5}$ and the solubility parameter of the carrier solvents was calculated to be 31 $Pa^{0.5}$ Example 5

A multi-purpose anti-itch lotion was prepared with the following recipe which includes an antihistamine:

Glycerol 10 ml, propylene glycol 50 ml; diethyleneglycolmonoethylether 5 ml; water 25 ml;

isopropanol 12.5 ml; methyl salicylate 3.75 ml; triethanolamine 3.75 ml; aloe vera emulsion 2 ml; oat oil 0.5 ml; sodium lauryl sulfate 25 mg; magnesium sulfate heptahydrate 0.5 gm; zinc acetate dihydrate 0.75 gm; calcium hydroxide 0.5 gm; aspirin 1 gm; methyl paraben 0.15 gm; benzethonium chloride 0.2 gm; salicylic acid 0.45 gm; benzocaine 0.75 gm; sodium bicarbonate 0.25 gm Cab-O-Sil M-5; 2 gm; oat colloid 0.5 gm; diphenhydramine hydrochloride 0.75 gm; sodium tetraborate 0.5 gm.

This formulation was particularly effective on a person with an unknown itch causation but who had found that an antihistamine pill taken orally concurrent with an evening application of a similar formulation (without diphenhydramine hydrochloride) had been more effective in relieving the itch than the lotion by itself. Addition of the diphenhydramine hydrochloride antihistamine was particularly effective in relieving the itch. The solubility parameter of the liquid mixture was 30.9 $Pa^{0.5}$ the pH was about 8.2 and the divalent cation concentration was about 0.11 molar Example 6 Trolamine salicylate solution was made by adding 69.1 grams of salicylic acid and 74.6 gm of triethanolamine to 50 ml of propylene glycol, and heating to 150° F. for 1 hour. Nine ml of this solution (4 gm of aspirin salicylate equivalent) was added to 50 ml isopropanol, 45 ml proypylene glycol, 100 mg sodium lauryl sulfate, 5 ml triethanolamine, 8 ml of Aloe Spring (20×), 4 grams of sodium tetraborate hydrate, 1 cm of calcium acetate hydrate, 2 gm of magnesium sulfate, 0.3 gm of zinc acetate, 0.5 gm of lidocaine, 0.8 gm benzethonium chloride, 2 ml of oat oil, 3.5 gm oat flour, 0.25 gm methyl paraben, 40 ml glycerin, 100 ml water and 1.0 gm of Kelco CG Xanthan. The pH of this mix was about 9. Its content of divalent metals was about 0.13 molar and its average solubility parameter was about 25.2.

Example 7

A multi-purpose skin lotion was prepared using: Glycerol 40 ml, propylene glycol 50 ml; water 100 ml; isopropanol 50 ml; triethanolamine 10 ml; aloe vera 20× emulsion 8 ml; oat oil 2.0 ml; sodium lauryl sulfate 100 mg; magnesium sulfate heptahydrate 2.0 gm; zinc acetate dihydrate 0.27 gm; calcium acetate hydrate 1.0 gm; aspirin 4 gm; lidocaine 0.50 gm; benzethonium chloride 0.80 gm; lidocaine 0.50 gm; xanthan gum 1.67 gm; oat colloid 3.2 gm; oat oil 2.0 ml; sodium tetraborate 3 gm. This semi-gelled formulation had a pH of 8.5-9. It had concentrations of multi-valent cations and solvent solubility parameters as noted in Table 5.

This formulation uniquely combines several chemicals that the Food and Drug Administration considers to be potential "active ingredients" in approved skin treatments, but uses them in lower concentrations such that the final product can be considered a cosmetic skin lotion rather than a medication, yet the additive and synergistic effects combined to make an effective anti-itch treatment as reported by a number of users.

Example 8

A simple formula was prepared emphasizing the combined effects of Epsom salts and aloe using 8.45 liters of glycerin, 20.0 liters of water, 211 grams of xanthan, 1.1 liters of 20× Aloe formulation (aloe gel+aloe liquid), 317 grams of Epsom salts and 422 ml of Phillips Milk of Magnesia containing magnesium hydroxide and sodium hypochlorite. This formulation had a pH about 9.0, a smooth viscosity comparable to that of skin lotions. Its soluble magnesium ion content was 0.043 molal, and its mixed solubility parameter was about 43.7 $Pa^{0.5}$. A similar formulation can be made without the 20 liters of water, giving a product with a higher concentration of the multivalent cation. This formulation was tested for viscosity and thixotropy in accordance with Method B of ASTM Standard D2196-10 with a Brookfield LVF viscosimeter, spindle LV3. At 6 rpm the viscosity was measured to be 5400 cps and at 60 rpm the apparent viscosity was 820 cps.

Example 9

A formulation comparable to that of Example 8 was made by adding 2% diphenhydramine hydrochloride, an anti-histamine which has been recommended for treatment of the painful withdrawal from Topical Steroid Addiction. The latter has been caused by long-term usage of cortisones on the skin for treatment of eczema or other diseases. This formulation has been found to be quite helpful, minimizing pain of a number of persons who stopped using cortisones, and it has helped to heal the actinic keratosis on legs of the inventor.

Example 10

A topical formulation was prepared for toughening fingernails and for helping to minimize problems of drying and splitting in conditions of low humidity, and for toughening the fingernails for baseball pitchers using the knuckleball grip. The formula added multi-valent cations to a solvent system of isopropanol and propylene glycol with the formula:

Isopropanol 5 ml; propylene glycol 20 ml; calcium nitrate hexahydrate 3.5 gm; xanthan gum 0.10 gm and water 5 ml. The mixed solubility parameter was 30.5 and the molal concentration of calcium was 0.48. This formulation was applied daily to fingernails on the left hand and was compared to the untreated fingernails of the right hand. Cracks and splits were noted to be about 50% less on the treated fingernails.

Xanthan gums have been found to provide sufficient thixotropy to suspend the colloidal oatmeal in formulations when used judiciously with high speed dispersion and with allowance of sufficient time for its partial gelation to be accomplished. Several examples use such a thickener, Keltrol CG from CP Kelco in Atlanta Ga. Xanthan does not give a sticky mix as does guar gum and it is less subject to an abrupt transition than with gelatin going from low viscosity to a hard gel with increasing concentration. Xanthan is best pre-soaked when dispersed in glycerin, then added to water with high speed stirring, sometimes warming to about 140° F. Formulations with xanthan gum are almost completely transparent when applied to the skin (certainly an attribute for treatment of facial acne) and do not leave a white powdery residue that transfers to clothing as occurs with fumed silica gellants.

These treatments have been used for continued treatment of actinic keratosis, as new spots have developed on various parts of the body. They have been effective in relieving the itch and for curing the keratoses in personal (non-clinical) applications. Various of the formulations have been found to be effective treatments of insect bites and stings, acne, topical steroid addiction, eczema, and unknown itch causes.

These examples of antipruritic formulations combine a number of chemicals in unique form, each performing multiple functions for this application. Glycerol and propylene glycol provide four attributes acting as solvents for the active ingredients, acting as carriers for transmitting the active ingredients into and through the skin, acting as humectants for preventing the skin from drying out and remaining in place with little evaporation. Triethanolamine is an effective solvent, an alkaline component and a smooth residual surface. The organic salts of divalent metals provide effective long-term anti-itch effects and may provide slight alkalinity. Methyl salicylate is thought to perform three functions—pain relief, solvency, and a pleasant medical aroma. A small amount of sodium hypochlorite is effective as an alkalinity (for neutralizing the acids of plant poisons), as a topical disinfectant, and a preservative during storage. This unique combination of such ingredients with other medicinals provides an effective multi-purpose anti-itch treatment.

The solubility parameters of mixed solvents and the molal concentrations of divalent cations as used in these Examples are presented in Table 5 as calculated by the formula noted above:

TABLE 5

Solubility Parameters and Molal Concentrations of Example Formulations

| Example | Solubility Parameter of Mixture, $Pa^{0.5}$ | | Molal Concentration of Multivalent Cations | |
|---|---|---|---|---|
| | Including Water | Carrier Solvents | Including Water | In Carrier Solvents |
| 1 | 21.6 | 18.0 | 0.75 | 0.75 |
| 2 | 35.2 | 35.2 | 0.39 | 0.39 |
| 3 | 33.6 | 26.0 | 0.25 | 0.31 |
| 4 | 30.5 | 26.4 | 0.25 | 0.31 |
| 5 | 30.9 | 26.9 | 0.11 | 0.14 |
| 6 | 25.2 | 24.2 | 0.13 | 0.18 |
| 7 | 34.8 | 25.7 | .058 | 0.10 |
| 8 | 43.7 | 33.7 | 0.043 | 0.11 |
| 9 | 43.7 | 33.7 | 0.043 | 0.11 |
| 10 | 30.5 | 24.9 | 0.48 | 0.59 |

The concentration of dissolved calcium ion in water of calamine lotion was noted above to be 0.022 mole per liter. The concentrations of multivalent cations in carrier solvents in Examples of Table 5 are noted to be 5 to 34 times the concentration in calamine lotion.

The solubility parameters and molal concentrations of multivalent cations in the carrier solvents are the more critical and unique characteristics of various embodiments disclosed herein, characteristics which have either been unknown or which have been ignored by other formulators of skin treatments. The carrier solvents transport the functional ingredients to nerve endings where they accomplish their functions; water is principally a diluent which evaporates readily and allows the other components to accomplish their desired effects.

The pH of an alcoholic solution is difficult to measure with a conventional glass electrode pH meter. An alternative is to titrate the "total base number" following procedures of ASTM D4739. A base number of 0.56 mg KOH/gram sample is about the same as pH=9, which is preferred for the multi-purpose skin lotions of various embodiments disclosed herein.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. A formulation of a transdermal skin treatment effective in inhibition of itch sensation, the formulation comprising:
   a solvent mixture of alcohols, glycols and water combined to provide a solubility parameter between 20 Pa0.5 and 40 Pa0.5, the solvent mixture having an average normal boiling temperature of at least 100° C., the solvent mixture having at least 0.04 mols/liter of multivalent cations, the solvent mixture containing at least one local anesthetic, and the solvent mixture having pH exceeding 8.0, with a thixotropic flow characteristic accomplished by an organic gellant, a colloidal oat flour, and the multivalent cations configured for delivery by the solvent mixture to allow the multivalent cations to penetrate an epidermis barrier with greater penetration than water so as to deliver the multivalent cations to nerve endings for the transdermal skin treatment effective in inhibition of itch sensations.

2. A formulation according to claim 1 wherein the formulation contains multivalent cation compounds, wherein the multivalent cation compounds are soluble in the solvent, mixture, and wherein the multivalent cation compounds have a total concentration exceeding 0.10 molar.

3. A formulation according to claim 2 wherein the medically acceptable multivalent cation compounds includes at least one of magnesium sulfate, calcium acetate, and zinc acetate.

4. A formulation according to claim 1 wherein the formulation contains a medically acceptable liquid analgesic.

5. A formulation according to claim 4 wherein the medically acceptable liquid analgesic is methylsalicylate.

6. A formulation according to claim 1 wherein the formulation contains a medically acceptable solid analgesic soluble in the carrier system.

7. A formulation according to claim 6 wherein the medically acceptable analgesic is acetyl salicyclic acid.

8. A formulation according to claim 1 wherein the formulation contains a medically acceptable liquid organic alkaline compound.

9. A formulation according to claim 8 wherein the medically acceptable liquid organic alkaline compound is triethanolamine.

10. A formulation according to claim 1 wherein the formulation contains an antibiotic soluble in the solvent mixture.

11. A formulation according to claim 10 wherein the antibiotic is benzethonium chloride.

12. A medically acceptable topical lotion comprising the formulation of claim 1 and containing gellant to provide a viscosity exceeding 400 centipoise.

13. A formulation according to claim 7 having a gellant including xanthan gum.

14. A formulation of claim 1 having a low viscosity suitable for pump or aerosol spray application.

15. A formulation according to claim 1 containing an anti-fungal ingredient.

16. A formulation according to claim 15 wherein the anti-fungal is one of tolnaftate, zinc undecylenate and zinc pyrithione.

17. A formulation according to claim 1 wherein the formulation contains anti-viral compounds.

18. A formulation according to claim 17 wherein the anti-viral compounds include at least one of acyclovir, famiclovir and valacyclovir.

19. A formulation according to claim 1 wherein the formulation contains Vitamins B-1 and B-12.

20. A formulation according to claim 1 further comprising pramoxin.

21. A formulation according to claim 1 further comprising pramoxin hydrochloride.

22. A formulation according to claim 1 further comprising an anti-fungal component.

23. A formulation according to claim 22 wherein the anti-fungal component includes at least one of zinc undecylenate, potassium sorbate, ciclopirox-ethanolamine, tolnaftate, and zinc pyrithione.

* * * * *